(12) United States Patent
Travkina et al.

(10) Patent No.: US 6,365,139 B2
(45) Date of Patent: *Apr. 2, 2002

(54) COSMETIC STICK

(75) Inventors: Irina Travkina, River Edge; Maha Raouf, Franklin Lakes; Harold Pahlck, Waldwick, all of NJ (US)

(73) Assignee: Avon Products, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/770,790

(22) Filed: Jan. 26, 2001

Related U.S. Application Data

(63) Continuation of application No. 09/226,303, filed on Jan. 7, 1999, now Pat. No. 6,183,760.
(60) Provisional application No. 60/083,528, filed on Apr. 29, 1998.

(51) Int. Cl.$^7$ .............................. A61K 6/00; A61K 7/00; A61K 7/025
(52) U.S. Cl. .......................... 424/64; 424/401; 514/844
(58) Field of Search ................... 424/64, 401; 514/844, 514/847

(56) References Cited

U.S. PATENT DOCUMENTS 6,183,760 B1 * 2/2001 Travkina et al. ............ 424/401

* cited by examiner

*Primary Examiner*—Thurman K. Page
*Assistant Examiner*—S. Howard
(74) *Attorney, Agent, or Firm*—Ohlandt, Greeley, Ruggiero & Perle, LLP

(57) ABSTRACT

There is provided a moisturizing cosmetic stick that moisturizes, has good wear, and full and even coverage. The stick comprises: about 1% to about 35% by weight water, about 0.1% to about 8% by weight of a gelling agent, about 1% to about 5% by weight of an emulsifier, about 5% to about 10% by weight of a hard wax, about 5% to about 25% by weight of a lipophilic polar solvent, about 1% to about 5% by weight of a clay, and about 5% to about 30% by weight of a bulking agent. The present invention is also directed to a process for making such a moisturizing stick.

42 Claims, No Drawings

COSMETIC STICK

CROSS-REFERENCE TO RELATED APPLICATION

This application claims priority from and is a continuation of U.S. patent application Ser. No. 09/226,303, filed Jan. 7, 1999. U.S. Pat. No. 6,183,760 which claims benefit to provisional application No. 60/083,528 filed Apr. 29, 1998.

BACKGROUND OF THE INVENTION

1. Field of the Invention

The present invention relates to a cosmetic stick. More particularly, the present invention is directed to a cosmetic stick for the lips and the skin ("both of which are called the lips" in this application) that has a high water content. Thus, the cosmetic stick can moisturize and at the same time protect the lips from damage.

2. Description of the Related Art

The incidence of ultraviolet and infrared radiation on the human epidermis is linked to exposure to sun, and also to the lamps and dryers used in hairdressing salons. Infrared radiation may give rise to a dense multiplication of fine elastic fibers in the upper dermis and induce carcinogenesis. Moreover, infrared radiation may cause vasodilation, raise skin temperature and cause skin erythema. To protect the lips from deleterious effects resulting from dryness, heat and infrared and ultraviolet radiation, as well as to produce a desired cosmetic effect, a moisturizing or water based lipstick is desired.

To manufacture a conventional lipstick; fats; oils; colorants, such as dyes, pigments or lakes; and, other non-aqueous ingredients are added to a wax base that is melted to enable the ingredients to be thoroughly mixed. Then, the mixed ingredients are cast into molds which, after cooling, provide the lipstick. In such a lipstick, water is not usually incorporated into the lipstick formulation. Therefore, the lipstick when applied to the lips does not necessarily possess the smooth, soft attributes associated with other skin treatment products having water, such as skin creams, particularly those intended for moisturizing the lips.

Thus, it is desired to provide a lipstick that has the moisturizing attributes of skin products rather than conventional water-free lipsticks.

U.S. Pat. No. 5,085,856 to Dunphy et al. discloses a cosmetic water-in-oil emulsion lipstick that requires, in addition to oil, wax, water and pigment, two or more emulsifiers including a phospholipid. U.S. Pat. No. 5,108,737 and 5,310,547, also to Dunphy et al., disclose a colored cosmetic lipstick and a method for coloring lips that comprises water, a low fatty acid wax and a colorant (an aluminum salt). However, the stick must be formulated with no higher than about 0.5% by weight of a C10 to C26 fatty acid or the lipstick would lose structure, and certain colorants, such as barium and calcium lakes cannot be used in this formulation.

U.S. Pat. No. 5,176,902 to Castro et al. discloses a colored cosmetic stick comprising a natural wax, a colorant, and a C12–C60 fatty acid ester that has no C12–C60 fatty acid. The wax is treated with a C1–C60 monohydric or polyhydric alcohol to convert any C12–C60 fatty acid to the corresponding ester and to produce an esterified wax.

U.S. Pat. No. 3,957,969 to Fujiyama is directed to a cosmetic stick comprising a water-in-oil emulsion. This stick has 1 to 50% water. According to this patent, a gel is prepared from a polyhydroxy compound and a non-ionic, surface active compound. This gel is mixed into a cosmetic base, and should produce a very soft pomade that would be difficult to manufacture.

U.S. Pat. No. 5,593,662 to Deckner et al. discloses a moisturizing lipstick essentially free of water.

Transparent lipsticks are disclosed in several patents. For example, U.S. Pat. No. 5,120,541 to Macaulay et al. discloses a transparent cosmetic stick composition having a lamellar structure that has a soap crystal growth inhibitor. U.S. Pat. No. 5,427,771 to Grollier et al. also discloses a transparent composition for the skin.

Examples of lipsticks that are based on silicone derivatives are disclosed in U.S. Pat. Nos. 5,750,095 and 5,556,613 to Arnaud et al., while U.S. Pat. No. 4,820,510 to Arraudeau et al. discloses an anhydrous cosmetic make-up composition.

U.S. Pat. No. 5,674,508 to Deserable et al. discloses a cosmetic composition for composing sticks for the lips or the skin comprising an anhydrous base in which a water-in-silicone emulsion is dispersed. The emulsion consists of an aqueous phase dispersed in a lipophilic phase comprising one or more silicones. U.S. Pat. No. 5,672,339 to Soyama et al. discloses a composition for rouge for lips containing a volatile oil content, such as volatile siloxanes and isoparaffins, and a water-repellent polymer. U.S. Pat. No. 5,505,937 to Castrogiovanni et al. discloses a lipstick composition that requires a silicone ester wax. U.S. Pat. No. 5,334,372 to Kawamata et al. discloses a cosmetic composition requiring an alcohol-modified silicone ester derivative of a formula recited in the claim. U.S. Pat. No. 5,288,482 to Krzysik is directed to a lipcare cosmetic composition that requires an alkylmethylpolysiloxane having a specific formula disclosed in the patent. U.S. Pat. No. 5,085,855 to Shore provides lip color formulations that require a dimethicone siloxane, from about 10% to 20% lanolin oil/stearalkonium hectorite gelling agent, and a hydrocarbon-derived polymer.

Other lipstick compositions are found in U.S. Pat. Nos. 5,753,240; 5,741,499; 5,466,457; 5,342,134; 5,197,814; 4,504,464; 4,492,686; 4,438,140; 3,957,969; 2,876,162 and 2,548,970; Belgian Patent No. 752,558 and Swiss Patent No. 519,913.

SUMMARY OF THE INVENTION

It is an object of the present invention to provide a cosmetic stick that has a high water content.

It is another object of the present invention to provide such a stick that has an even and full coverage, high shine, and good wear properties.

It is still another object of the present invention to provide such a stick that is not sticky to the touch, has good chemical and photochemical stability and adhesion to the lip or skin, and does not leave a white film on the lip.

It is a further object of the present invention to provide such a stick that moisturizes, has a wet feel on the lips, and the ability to incorporate water soluble ingredients into a stick, such as a lipstick, balm, pomade or pot.

It is a still further object of the present invention to provide a process for making the moisturizing cosmetic stick that is easy to commercialize.

These and other objects of the present invention are provided by a cosmetic stick that comprises a high content of water, a gelling agent, an emulsifier, a hard wax, a lipophilic solvent, a clay and a bulking agent.

The present invention further provides a method of protecting the lips against the harmful effects of dryness, heat and infrared and ultraviolet radiation. The method comprises the application of the cosmetic stick of the present invention onto the lips.

DETAILED DESCRIPTION OF THE INVENTION

The cosmetic stick of the present invention can be a stick, such as a lipstick, pomade, balm, pot or other stick (hereinafter collectively called "stick"). Preferably, it is a lipstick. The stick has improved moisturizing properties, as well as good wear, even and full coverage, high shine, adhesion, good chemical and photochemical stability, and does not leave a white film. Also, the stick has a wet and cooling feel once applied and the ability to incorporate water soluble ingredients. The above benefits are achieved by the ability to have a stick with a high water content. As discussed below, the water content is preferably about 15% to about 25% by weight of the stick.

The cosmetic stick basically includes a water phase, an oil phase and, if desired, a fragrance. The water phase includes water, a gelling agent and, preferably, a humectant and a moisturizer. The oil phase includes the other ingredients of the stick, except for the fragrance, if any, The water forms the majority of the water phase and provides a solvent for any water-soluble ingredients present in the moisturizing stick, which is called herein a hydrostick. The water is preferably demineralized water. The amount of water present is from about 1% to about 35% by weight of the stick. Preferably, water is present in an amount from about 15% to about 35%, more preferably about 15% by weight to about 25% by weight, and most preferably about 20% by weight of the stick. It is this high water content that provides many benefits of the present stick.

The gelling agent, the second ingredient in the water phase, is about 0.1% to about 8% by weight, preferably about 0.1% to about 5% by weight of the stick. However, the gelling agent is more preferably about 1.5% to about 2.5% by weight of the stick. The gelling agent can be, for example, one or more polymethacrylates, carbomers, cellulosics, water swellable Lucentite SWN, and Vee gums. The preferred gelling agent is glyceryl polymethacrylate.

As stated above, the water phase may include one or more humectants and moisturizers. The humectants and moisturizers are about 0.001% to about 10% by weight, preferably about 1.0% to about 3.0% by weight, and more preferably about 1.6% by weight of the stick. The preferred humectant is glycerin. The preferred moisturizer is hyaluronic acid sodium salt.

The ratio of water phase to the oil phase is 2:3 to 1:5. The water phase is preferably about 25% by weight of the stick, while the oil phase is preferably about 75% by weight of the stick. The oil phase includes one or more emulsifiers, hard wax, lipophilic solvent, clay and bulking agents, such as powder fillers. The oil phase may include other ingredients such as waxes, preservatives, bulking agents and colorants.

The emulsifier acts to uniformly disperse the ingredients. The emulsifier is about 1% to about 5% by weight of the stick. Preferably, the emulsifier is about 2% by weight of the stick.

The emulsifiers suitable for use in the present invention are preferably polyglyceryl fatty acid esters, and secondary emulsifiers, such as fatty acid alcohols. Such emulsifier systems include polyglyceryl-10 pentastearate/behenyl alcohol.

The present invention includes one or more hard waxes, preferably with a high melting point, namely greater than 80 degrees C. A hard wax is one having a needle penetration (mm/10) in the range of 2 to 8 based on ASTM-D-1321. The hard wax of the present invention is present in an amount about 5% to about 10% by weight of the stick. Preferably, it is about 7% by weight of the stick. The hard wax is preferably polyethylene, more preferably linear polyethylene, and ozokerite. Thus, the most preferred hard wax is a combination of linear polyethylene and ozokerite.

The present stick may include other waxes in the oil phase. For example, these waxes include natural waxes, and paraffin and synthetic waxes. Such waxes include, but are not limited to: candelilla, micro wax, beeswax, and mixtures thereof. The total amount of these other waxes if present in the hydrostick is about 3% to about 4% by weight of the stick.

The present stick also includes a lipophilic polar solvent in its oil phase. This solvent is present in an amount about 5% to about 25% by weight of the stick, preferably about 19% by weight of the stick. The preferred lipophilic polar solvent is a C12–15 alcohol benzoate.

The oil phase of the present stick also includes a thickener/gelling agent and a bulking agent that act as structure-enhancing agents. These agents provide body and strength to the moisturizing hydrostick thereby making it free-standing and capable of retaining its original shape. This attribute is especially helpful in the commercialization since the stick must maintain its structure.

A structure-enhancing agent suitable for use in the moisturizing hydrostick of the present invention is a clay. The clays include lithium magnesium silicate also known as smectite clay, bentonite clay, also known as wilkinite, montmorillonite represented by the formula $Al2O3.4SiO2.H2O$, and mixtures thereof. Lithium magnesium silicate or smectite clay is preferred.

Smectite clays can be natural or synthetic. Synthetic smectite clays are preferred over the naturally occurring varieties since they typically have a lower impurity content. Such synthetic smectite SAN clay is distributed by Kobo Products Inc. and manufactured by Nikko Chemicals Co., Ltd. Kobo Products Inc. have disclosed the structure of their synthetic smectite clay, called Lucentite SAN, as including 60.00 to 70.00 percent lithium magnesium sodium silicate having the following empirical formula: $(Na0-0.33 (Mg2.67Li0.33)(Si4O4)(OH)2)$ and 30.00 to 40.00 percent quaternium-18 ($[R2N(CH3)2]$, where R is C16–C18 alkyl). Kobo Products Inc. have also stated that quaternium-18 is not reacted with lithium magnesium sodium silicate to form the Lucentite SAN.

The smectite clay has the property of forming highly viscous suspensions or gels. The smectite clay is preferably gelled with a polar lipophilic hydrocarbon-based solvent. The most preferred solvents contain an aromatic group, namely benzoate esters, such as C12–15 alcohols benzoate (Finsolv TN), and salicylate esters. However, the solvent C12–15 alcohol lactate is also preferred, since it also swells the synthetic smectite effectively.

Preferably, the amount of the smectite clay in the moisturizing hydrostick of the present invention is from about 1% to about 5% by weight of the stick. More preferably, the amount of the smectite clay is about 2% by weight of the stick.

The bulking agents add structure enhancing properties to the stick. Such bulking agents include mica, barium sulfate, nylon, talc, starch, calcium carbonate, silica, and mixtures thereof. The bulking agents and colorants are present in an amount about 5% to about 30% by weight, and preferably about 5% to about 15% by weight of the stick. The bulking agent is more preferably present in an amount about 11% of the stick. Colorants and pigments in powder form may also function as bulking agents. Such colorants include, for example, inorganic and organic colorants, such as barium lakes, calcium lakes, aluminum lakes, titanium dioxide, mica and iron oxides. It has been found that the present stick does not limit the use of the type of colorants, unlike prior art water containing lipsticks.

The hydrostick with the smectite clay and bulking agent has superior stick integrity and lattice strength, even at reduced wax levels. This imparts to the finished stick a smooth and creamy consistency. Moreover, the compositions containing the agents do not need to be extruded or compressed to form a cake or stick. The finished stick has improved stability over time and over a wide range of temperatures thus facilitating commercialization. In addition, clear, true colors can be provided.

A fragrance and/or flavor may be included in the present stick in an amount about 0.1% to about 2.0% by weight of the stick. As stated above, the fragrance and/or flavor preferably is neither in the oil nor the water phase, but is added separately.

The water and the oil phases provide the cosmetic stick with about 1% to about 35% by weight water, about 0.1% to about 8% by weight of the gelling agent, about 1% to about 5% by weight of the emulsifier, about 5% to about 10% by weight of the hard wax, about 5% to about 25% by weight of the lipophilic polar solvent, about 1% to about 5% by weight of the clay, and about 5% to about 30% the bulking agent.

The moisturizing hydrostick of the present invention may contain other ingredients in the oil phase, such as, for example, one or more pigments, thickeners, skin protectants, preservatives or stabilizers, and vitamins. The hydrostick may also include one or more perfumes, antioxidants, UV-absorbers (e.g. screening agents or sunscreens), germicides, and lipid materials.

The present invention may include one or more emollients. The total amount of the emollients present is about 20% to about 25% by weight of the stick.

The preferred emollients include: polytriglyceryl erucate/eleostearate, avocado, lanolin, preferably low odor, diisostearyl fumarate, myristyl lactate, and mixtures thereof. The polytriglyceryl erucate/eleostearate is a film forming emollient that is preferable as an emollient in the present stick. This particular emollient is present in an amount about 5% to about 10% by weight, and preferably about 6.5% by weight of the stick.

The present stick may also include one or more preservatives. These preservatives are present in an amount about 0.1% to about 3% by weight, and preferably about 0.5% by weight of the stick. Preferred preservatives include: EDTA, iodopropynylbutyl carbamate, 4-hydroxybenzoic acid, its esters and derivatives, such as methyl 4-hydroxybenzoate (methyl paraben), ethyl 4-hydroxybenzoate (ethyl paraben), propyl 4-hydroxybenzoate (propyl paraben) and butyl 4-hydroxybenzoate (butyl paraben). The most preferred preservatives include methyl paraben, propyl paraben and iodopropynylbutyl carbamate, and mixtures thereof.

The formula may also contain UV stabilizers and antioxidants, such as BHT, BHA, benzophenones such as: 2,4-dihydroxybenzophenone, 2,2'-dihydroxy-4-methoxybenzophenone, 2,2'-dihydroxy-4,4"-dimethoxybenzophenone, 2,2'-dihydroxy-4,4'-dimethoxybenzophenone-5-sulphonic acid and its salts, 2,2', 4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulphonic acid and its salts, 4-phenylbenzophenone, 2-ethylhexyl-4'-phenylbenzophenone-2-carboxylate, 2-hydroxy-4-n-octyloxybenzophenone and 4-hydroxy-3-benzophenonecarboxylic acid and its salts; benzotriazole derivatives such as 2-(2'-hydroxy-5'-methylphenyl)-2H-benzotriazole, 2-(2'-hydroxy-5'-tert-octylphenyl)-2H-benzotriazole, 2-(2'-hydroxy-3',5'-di-tert-octylphenyl)-2H-benzotriazole, 2-(2'-hydroxy-5'-cumylphenyl)-2H-benzotriazole and 2-(2'-hydroxy-3',5'-di-cumylphenyl)-2H-benzotriazole; disubstituted methane derivatives such as dianisoyl methane, 4-isopropyl dibenzoyl methane and 4-tert-butyl-4'-methoxy dibenzoyl methane.

The present stick may include a skin protectant, such as, for example, allantoin. Allantoin would be present in an amount about 0.1% to about 3% by weight, and preferably in an amount about 0.55% by weight of the stick.

The preferred stick may also include vitamins, such as, for example, tocopheryl acetate (vitamin E), and vitamins A and C, and beta carotene. Such vitamins are present in an amount about 0.1% to about 3% by weight, and preferably in an amount about 0.55% by weight of the stick.

The hydrostick of the present invention can take the form of a solid stick, such as, a lipstick, pomade, balm, pot, lip-gloss or of a cream that can be applied to the skin or the lips.

The present stick permits the use of high acid value substances, such as natural oils and waxes, having up to 2% free fatty acids without the stick losing its structure. In addition, the present stick, especially when used as a lipstick, provides a wet, cool, smooth refreshing or creamy feel, and applies evenly. Still further, the present stick can be made using conventional lipstick molding equipment.

The present invention includes a process for preparing the moisturizing hydrostick. The process includes forming the oil phase and the water phase, separately. Then, the two phases are mixed together until uniform, the fragrance/flavor is added and then poured into in a single row cavity or a single cavity mold. The mold should then be chilled at a low temperature, namely about 35 to about 40 degrees F., for a short period of time, namely less than ten minutes. This chilling process is important for the production of the final stick.

The hydrostick of the present invention is suitable for the lips, especially for applying to the lips a long lasting color with pleasant aesthetics to the lips. The hydrostick can also be used as a vehicle for a skin care agent to protect against exposure to adverse weather, including the wind and rain or extended exposure to sunlight.

The present invention is further illustrated by the following example, which is designed to illustrate the invention without limiting its scope.

Obvious modifications and variations of the invention can be made without departing from the scope of the present invention as defined by the appended claims.

Wherefore we claim:

1. A moisturizing cosmetic stick comprising:
   a water phase being about 1% to about 40% by weight of the stick, said water phase having water and a gelling agent, wherein said water is in an amount about 15% to about 35% by weight of the stick; and
   an oil phase being about 60% to about 99% by weight of the stick.

2. The stick of claim 1, wherein said oil phase includes, based on the weight of the stick, about 1% to about 5% by weight of an emulsifier, about 5% to about 10% by weight of a hard wax, about 5% to about 25% by weight of a lipophilic polar solvent, about 1% to about 5% by weight of a clay, and about 5% to about 30% by weight of a bulking agent.

3. The stick of claim 1, further comprising one or more waxes and colorants.

4. The stick of claim 1, wherein said gelling agent is about 1.5% to about 2.5% by weight of the stick.

5. The stick of claim 1, wherein said gelling agent is glyceryl polymethacrylate.

6. The stick of claim 1, further comprising an emulsifier, the emulsifier being a polyglyceryl fatty acid ester.

7. The stick of claim 1, further comprising a hard wax selected from the group consisting of polyethylene, ozokerite and mixtures thereof.

8. The stick of claim 1, further comprising a wax selected from the group consisting of natural waxes, paraffins and synthetic waxes.

9. The stick of claim 1, further comprising a lipophilic polar solvent, the solvent being a C12–15 alcohol benzoate.

10. The stick of claim 1, further comprising a clay selected from the group consisting of lithium magnesium silicate, bentonite, montmorillonite, and mixtures thereof.

11. The stick of claim 1, wherein said clay is about 1% to about 3% by weight of the stick.

12. The stick of claim 1, wherein said bulking agent is selected from the group consisting of nylon, talc, starch, calcium carbonate, silica, barium sulfate, mica and mixtures thereof.

13. The stick of claim 1, further comprising a colorant that is selected from the group consisting of calcium lakes, barium lakes, aluminum lakes, titanium dioxide, iron oxides, and mixtures thereof.

14. The stick of claim 1, wherein the stick is a lipstick.

15. A process for making a moisturizing stick comprising:
forming an oil phase;
forming a water phase;
mixing the oil phase and the water phase together in a mold; and
chilling the mold at a temperature about 35 to about 40 degrees F., for less than ten minutes to form the stick.

16. A moisturizing cosmetic stick comprising:
a water phase being about 1% to about 40% by weight of the stick, said water phase having water and a gelling agent, wherein said gelling agent is in an amount about 0.1% to about 8% by weight of the stick; and
an oil phase being about 60% to about 99% by weight of the stick.

17. The stick of claim 16, wherein said gelling agent is about 0.1% to about 5% by weight of the stick.

18. The stick of claim 1, wherein said water is in an amount from about 15% to about 25% by weight of the stick.

19. The stick of claim 1, wherein said gelling agent is in an amount about 0.1% to about 5% by weight of the stick.

20. The stick of claim 1, wherein said gelling agent comprises one or more ingredients selected from the group consisting of polymethacrylates, carbomers, cellulosics, water swellable Lucentite SWN, Vee gums and any combinations thereof.

21. The stick of claim 20, wherein said ingredient is a polymethacrylates.

22. The stick of claim 1, further comprising at least one ingredient selected from the group consisting of humectants, moisturizers, fragrances, waxes, emulsifiers, lipophilic solvents, clays, bulking agents, preservatives, moisturizers, fragrances, flavors, vitamins, UV absorbers, UV stabilizers, antioxidants, lipid materials, skin protectants, colorants and combinations thereof.

23. The stick of claim 22, wherein said ingredient is a wax selected from the group consisting of a hard wax, a natural wax, a paraffin, a synthetic wax, and combinations thereof.

24. The stick of claim 22, wherein said ingredient is a wax selected from the group consisting of polyethylene, ozokertite, candelilla, micro wax, beeswax and combinations thereof.

25. The stick of claim 23, wherein said wax is a hard wax and said hard wax is about 5% to about 10% by weight of the stick.

26. The stick of claim 23, wherein said wax is a hard wax and wherein said hard wax is a linear polyethylene or an ozokerite.

27. The stick of claim 23, wherein said wax is a hard wax and said hard wax is a linear polyethylene and an ozokerite.

28. The stick of claim 22, further comprising an ingredient selected from the group consisting of said humectant, said moisturizer and a combination thereof.

29. The stick of claim 28, wherein said ingredient is said humectant and said moisturizer and said humectant is glycerin and said moisturizer is hyaluronic acid sodium salt.

30. The stick of claim 1, wherein the ratio of said water phase to said oil phase is from 2:3 to 1:5.

31. The stick of claim 22, wherein said ingredient is an emulsifier and wherein said emulsifier is about 1% to about 5% by weight of the stick.

32. The stick of claim 22, wherein said ingredient is an emulsifier and wherein said emulsifier is polyglycerol-10 pentastearate/behenyl alcohol.

33. The stick of claim 22, wherein said ingredient is a lipophilic solvent and wherein said lipophilic solvent is about 5% to about 25% by weight of the stick.

34. The stick of claim 22, wherein said one or more clays comprises a smectite clay.

35. The stick of claim 34, wherein said smectite clay is gelled with a polar lipophilic hydrocarbon-based solvent.

36. The stick of claim 34, wherein said smectite clay is present from about 1% to about 5% by weight of the stick.

37. The stick of claim 22, wherein said ingredient is an emollient and wherein said emollient is a film-forming emollient.

38. The stick of claim 37, wherein said film-forming emollient is polytriglyceryl erucate/eleostearate.

39. The stick of claim 28, wherein said film-forming emollient is present from about 5% to about 10% by weight of the stick.

40. The stick of claim 22, wherein said ingredients are said UV stabilizers and antioxidants, said UV stabilizers and antioxidants being selected from the group consisting of BHT, BHA, 2,4-dihydroxybenzophenone, 2,2'-dihydroxy-4-methoxybenzophenone, 2,2'-dihydroxy-4,4"-dimethoxybenzophenone, 2,2'-dihydroxy-4,4'-dimethoxybenzophenone-5-sulphonic acid and its salts, 2,2', 4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulphonic acid and its salts, 4-phenylbenzophenone, 2-ethylhexyl-4'-phenylbenzophenone-2-carboxylate, 2-hydroxy-4-n-octyloxybenzophenone and 4-hydroxy-3-benzophenonecarboxylic acid and its salts, 2-(2'-hydroxy-5'-methylphenyl)-2H-benzotriazole, 2-(2'-hydroxy-5'-tert-octylphenyl)-2H-benzotriazole, 2-(2'-hydroxy-3',5'-di-tert-octylphenyl)-2H-benzotriazole, 2-(2'-hydroxy-5'-cumylphenyl)-2H-benzotriazole and 2-(2'-hydroxy-3',5'-di-cumylphenyl)-2H-benzotriazole, dianisoyl methane, 4-isopropyl dibenzoyl methane, 4-tert-butyl-4'-methoxy dibenzoyl methane and combinations thereof.

41. The stick of claim 1, wherein the stick is in a product form selected from the group consisting of a lipstick, a pomade, a balm, a pot, a lip gloss and a cream.

42. The stick of claim 1, further comprising up to 2% free fatty acids.

* * * * *

UNITED STATES PATENT AND TRADEMARK OFFICE
CERTIFICATE OF CORRECTION

PATENT NO. : 6,365,139 B2
DATED : April 2, 2002
INVENTOR(S) : Travkina et al.

It is certified that error appears in the above-identified patent and that said Letters Patent is hereby corrected as shown below:

Column 8,
Line 37, please change "The stick of claim 28, wherein said film-forming emollient..." to -- The stick of claim 38, wherein said-film-forming emollient... --

Signed and Sealed this

First Day of October, 2002

Attest:

Attesting Officer

JAMES E. ROGAN
Director of the United States Patent and Trademark Office